(12) United States Patent
Staal (10) Patent No.: US 6,187,595 B1
(45) Date of Patent: Feb. 13, 2001

(54) METHOD FOR DETECTING POLYMERS IN A SOLUTION, DETECTOR SYSTEM AND CHROMATOGRAPHY APPARATUS CONTAINING SUCH A DETECTOR SYSTEM

(75) Inventor: Willem Jacob Staal, Hoogerheide (NL)

(73) Assignee: Waters Investments Limited

( * ) Notice: Under 35 U.S.C. 154(b), the term of this patent shall be extended for 0 days.

(21) Appl. No.: 08/700,492

(22) PCT Filed: Mar. 6, 1995

(86) PCT No.: PCT/NL95/00084

§ 371 Date: Oct. 29, 1996

§ 102(e) Date: Oct. 29, 1996

(87) PCT Pub. No.: WO95/23966

PCT Pub. Date: Sep. 8, 1995

(30) Foreign Application Priority Data

Mar. 4, 1994 (EP) .................................................. 94200562

(51) Int. Cl.[7] ........................... G01N 21/00; G01N 21/17
(52) U.S. Cl. ....................... 436/161; 422/82.05; 210/656; 250/576
(58) Field of Search ............................ 436/161; 210/656, 210/739; 528/503; 250/576; 422/82.05

(56) References Cited

U.S. PATENT DOCUMENTS

| | | | | |
|---|---|---|---|---|
| 3,899,688 | * | 8/1975 | Périères | 250/576 |
| 4,988,630 | * | 1/1991 | Chen et al. | 436/533 |
| 5,080,798 | * | 1/1992 | James | 210/656 |
| 5,185,429 | * | 2/1993 | Cinquina et al. | 528/503 |
| 5,290,520 | * | 3/1994 | Maystre et al. | 422/82.05 |
| 5,405,879 | * | 4/1995 | Uemae et al. | 523/201 |
| 5,413,719 | * | 5/1995 | Sivakumar et al. | 210/708 |
| 5,430,116 | * | 7/1995 | Kramer et al. | 526/284 |
| 5,643,462 | * | 7/1997 | Chen et al. | 210/730 |

OTHER PUBLICATIONS

Maniatis, et al. in Molecular Cloning: A Laboratory Manual. pp. 64 and 80–82, Cold Spring Harbor Laboratory, Cold Spring Harbor, NY, 1982.*

Merriem–Webster, s Collegiate Dictionary, Tenth Edition, Merriam–Webster, Inc., p. 903, 1996.*

Zhu et al. 1992 J. Chromatog. 608, 225–237.*

* cited by examiner

Primary Examiner—Yvonne Eyler
Assistant Examiner—Nirmal S. Basi
(74) Attorney, Agent, or Firm—Anthony J. Janiuk (57) ABSTRACT

A method of quantitatively detecting a polymer in a solution of the polymer in a solvent is provided, which method comprises the steps of (a) adding to the solution a non-solvent for said polymer in a sufficient amount to make the resulting liquid turbid and (b) measuring the turbidity of the resulting liquid. A detecting device for detecting a polymer in a polymer-containing solution is also provided, which device comprises a line for supplying polymer-containing solution, a line for supplying non-solvent, a mixing chamber, a line connected to said mixing chamber for conveying the mixed liquid, and a detector for measuring turbidity in the mixed liquid, as well as an HPLC apparatus comprising a liquid separation system, especially a Gradient Polymer Elution Chromatography (GPEC)® system, connected to said detecting device.

14 Claims, 6 Drawing Sheets fig-1 fig-2

Fig. 3 fig-4 fig-5 fig-9 fig-10

METHOD FOR DETECTING POLYMERS IN A SOLUTION, DETECTOR SYSTEM AND CHROMATOGRAPHY APPARATUS CONTAINING SUCH A DETECTOR SYSTEM

The present invention is in the field of analytical methods and equipment. The invention relates to a method of detecting polymers in a solution of the polymer in a solvent.

Polymers can be analysed, qualitatively and quantitatively, using liquid chromatography techniques. The polymers can be separated e.g. on the basis of their molecular weight or size, charge or solubility. The polymers thus separated must subsequently be detected. In HPLC (High Performance Liquid Chromatography) detection is performed using flow-through detectors. The most common detectors are based on the absorption or emission of Ultraviolet (UV) or visible light (VIS) or the emission of fluorescent light.

A disadvantage of UV/VIS detectors for the detection of polymers is that they cannot detect polymers that do not absorb in the UV/VIS frequency range (about 190–800 nm). Also, UV/VIS absorbing solvents cannot be used with these detectors, since they drastically lower the sensitivity of the detection.

Other types of detectors that can be used for assaying polymers include moving belt detectors, flame ionisation detectors (FID) and evaporative light scattering detectors (ELSD). The major disadvantage of these types of detectors is that they are destructive to the sample. Refractive index detection is also frequently used, but it suffers from a low sensitivity and is not applicable with gradient elution.

U.S. Pat. No. 4,983,528 describes a method for determining the amount of unsaturation in an unsaturated elastomeric polymer by subjecting a solution sample of the polymer to gel permeation chromatography and measuring the absorption of UV radiation of 220 nm by the eluted sample. This method does not allow a determination of the amount of polymer which is independent on the degree of unsaturation of the polymer.

U.S. Pat. No. 5,129,723 discloses a method for deriving the molecular weight and other polymer parameters by injecting and mixing a suspension of the polymer into a HPLC tubing and measuring the scattering by a laser-irradiated volume of the suspension. This method is not suitable for determining the amount of polymer, nor for the separation and assaying of polymer.

The most common type of separation and detection of polymers used until now is gel permeation chromatography, combined with detection based on change of refractive index of the eluted sample. However, this method suffers from a poor resolution (inherent to gel permeation chromatography), and a low sensitivity (inherent to refractive index detection).

The object of the present invention is to provide a method and a device for detecting polymers in liquid chromatography techniques in a non-destructive way, without restrictions on the type of polymer or on the solvent to be used.

The method according to the invention for quantitatively detecting a polymer in a solution of the polymer in a solvent, is characterised by carrying out the steps of (a) adding to the solution a non-solvent for said polymer in a sufficient amount to make the resulting liquid turbid and (b) measuring the turbidity of the resulting liquid.

With the method of the present invention, the polymer solution is transformed into a polymer suspension. UV/VIS and fluorescence detectors can detect any kind of polymer in such a suspension, regardless of the type of solvent. Thus the present method has the following important advantages:

=universal applicability: no limitations on polymers, even nonabsorbing polymers such as polydimethylsiloxane can be measured, and even strongly UV-absorbing solvents such as benzene can be used;
=high sensitivity: UV/VIS and fluorescence detectors can detect turbidity with high efficiency;
=high resolution (selectivity): addition of different amounts and/or of different non-solvents allows separation of the polymers to be very finely tuned.

The types of polymers that can be assayed using the detecting system according to the present invention include e.g. polyethylene, polypropylene, poly(vinyl chloride), poly (vinyl acetate), polystyrene, poly(methyl methacrylate), poly(vinyl acetate), polydimethylsiloxane, polyols, which are all non UV/VIS-absorbing polymers, polyamides, polyesters, polycarbonates, polyurethanes, copolymers such as butadienestyrene copolymers, ABS, block copolymers, terpolymers, biopolymers such as polysaccharides, polypeptides etc.

In the present specification, a solvent is understood to be a liquid wherein the polymer to be assayed is essentially soluble.

Suitable solvents for the relatively apolar polymers include e.g. tetrahydrofuran, dioxane, other cyclic or acyclic ethers, dichloromethane, chloroform, other haloalkanes, dimethylformamide, aromatic hydrocarbons such as benzene or toluene, cyclohexane, and mixtures thereof. Suitable solvents for the relatively polar polymers include e.g. water, methanol, ethanol, acetonitrile, and mixtures thereof. The appropriate choice of solvent can be made by the skilled person on the basis of the type of polymer present in the test sample.

A non-solvent according to the invention as a liquid wherein the polymer to be assayed is essentially insoluble, and which, when added to a solution of the polymer, causes the polymer to become undissolved. The non-solvent to be used should be miscible with the solvent of the polymer solution. The appropriate choice of non-solvent can be made by the skilled person on the basis of the type of polymer present in the test sample and of the solvent used.

Suitable examples of non-solvents that can be used in combination with solvents such as tetrahydrofuran, dioxane, dichloromethane, chloroform, dimethylformamide or cyclohexane, include water, methanol, acetonitrile, hexane and isooctane. Suitable examples of non-solvents that can be used in combination with solvents such as water, methanol or acetonitrile include tetrahydrofuran, dioxane and dimethylformamide.

The non-solvent is added to the polymer solution e.g. by means of a HPLC pump. The solution thereby turns into a cloudy, turbid suspension. If necessary for preventing adhesion of the polymer suspension on the walls of the liquid lines, a detergent, in particular a nonionic detergent may be added to the non-solvent. The non-solvent is added in an amount which is sufficient to insolubilise the polymer to be assayed. By adding only a low amount of non-solvent the detecting system can detect polymers selectively. Only one or a few types of polymers become suspended and detectable, while the other polymers remain dissolved and are not detected. A distinction can thus be made, both according to the different chemical nature of the polymers, and according to their molecular weight.

It is sometimes advantageous to cool the polymer-containing solution before adding the non-solvent. Such cooling will result in a reduced solubility of one or more of the polymers and thus in an enhanced turbidity. This enhanced turbidity allows a more selective detection and/or a reduced consumption of non-solvent. The polymer-containing solution is preferably cooled to below 0° C., in particular to about −10° C.

Preferably, both tire polymer solution and the non-solvent are used in a continuous flow, such as in a liquid chromatography system. The turbidity of the suspension resulting from addition of non-solvent to the polymer solution is preferably measured using a UV/VIS detector or a fluorescence detector. A UV/VIS detector measures the light transmitted through the turbid suspension at wavelengths of e.g. 190–600 nm. A fluorescence detector measures the light emitted by the suspension at a 90° angle at wavelengths of e.g. 200–700 nm. Typical settings for fluorescence are an excitation at 350 nm and an emission at 360 nm.

The invention also relates to a detection device for detecting a polymer in a polymer-containing solution, comprising a line provided with a pump for supplying polymer-containing solution, a line provided with a pump for supplying non-solvent, a mixing chamber connected to said lines for mixing the non-solvent with the polymer-containing solution, a line connected to said mixing chamber for conveying the mixed liquid, and a detector for measuring turbidity in the mixed liquid. The detector can be of the UV/VIS or fluorescence types mentioned above.

The detecting system according to the invention is especially suitable for use in liquid chromatography. The invention also relates to a liquid chromatography apparatus comprising a liquid separation system connected to the detecting device described above. The chromatography technique may be e.g. gel filtration chromatography, gel permeation chromatography, size exclusion chromatography, ion chromatography, protein liquid chromatography, capillary zone electrophoresis or gradient polymer elution chromatography (GPEC).

The latter type of chromatography is particularly useful for assaying polymers of widely varying nature. It is an HPLC technique, wherein a sample containing 0.001 to 1% (v/v) of polymer in a suitable solvent is injected (injection volumes e.g. 1 to 200 $\mu$l). The solution is then turned into a turbid polymer suspension by addition of a non-solvent through a gradient pump. The polymer suspension is subsequently adsorbed on a solid-absorbing column, a so-called guard column. After adsorption, the gradient pump adds solvent to the guard column in order to dissolve the polymer from the column. At a certain solvent/non-solvent ratio the polymer dissolves and is eluted from the guard column. The separation is based on the difference in the redissolution solvent composition of the different polymers. The redissolved polymer is then transported to an analytical column for further separation. Thereafter non-solvent is added in order to make the separated polymer detectable, as detailed above. The mixing of the non-solvent and the polymer solution is performed e.g. using a high-pressure noise filter.

Figure 1:
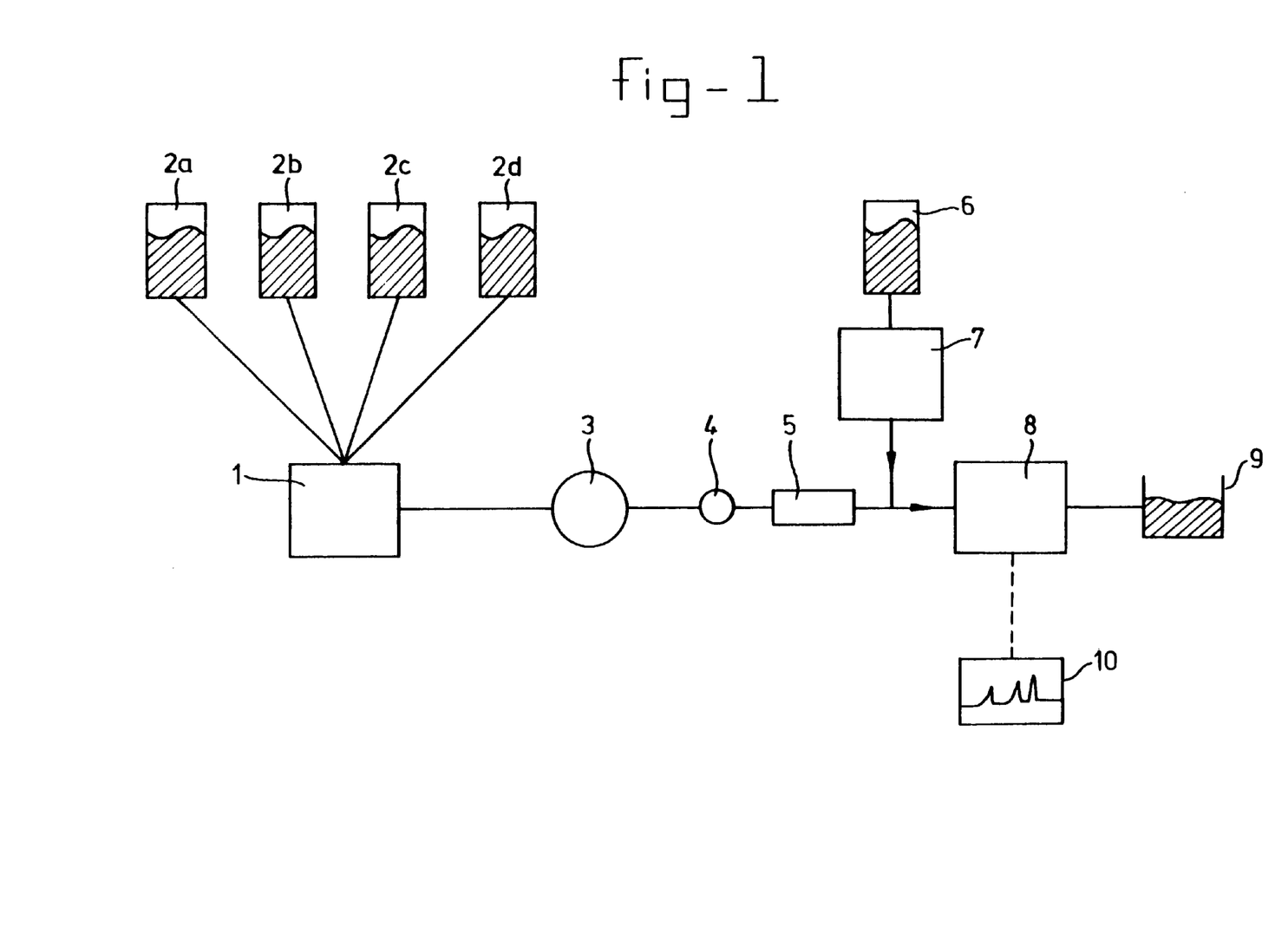
FIG. 1 depicts in schematic form an apparatus depicting features of the present invention.

The method and apparatus according to the invention are further described with reference to the accompanying FIG. 1. FIG. 1 shows a gradient pump (1), fed from a plurality of solvent containers (2a–2d). These containers hold e.g. three different solvents and a non-solvent respectively.

The gradient pump is connected with an injector (3) and subsequently with a guard column (4), wherein polymer may be absorbed and desorbed. The guard column is connected downstream with an analytical column (5). A non-solvent container (6) is connected through an isocratic pump (7) with the outlet of column (5). Downstream of both column (5) and pump (7), a UV or fluorescence detector (8) is located, which is then connected with a liquid collector (9). The detector is connected to a processing and/or recording system (10).

EXAMPLE 1

A sample of polydimethylsiloxane (PDMS) in tetrahydrofuran (THF) was assayed using the apparatus depicted in FIG. 1. PDMS, when dissolved in THF, is a non-absorbing polymer in the UV/VIS range. Water is a nonsolvent (precipitant) for PDMS. At 8% water addition, the polymer is precipitated.

Chromatography was performed using the following characteristics:

Gradient: Water/THF (50/50) to THF in 15 min., curve linear

Flow: 1 ml/min

Column: NovaPak CN

Turbidity detector: UV/VIS 550 nm

Turbidity liquid: Water+nonionic detergent; flow 3 ml/min.

Figure 2:
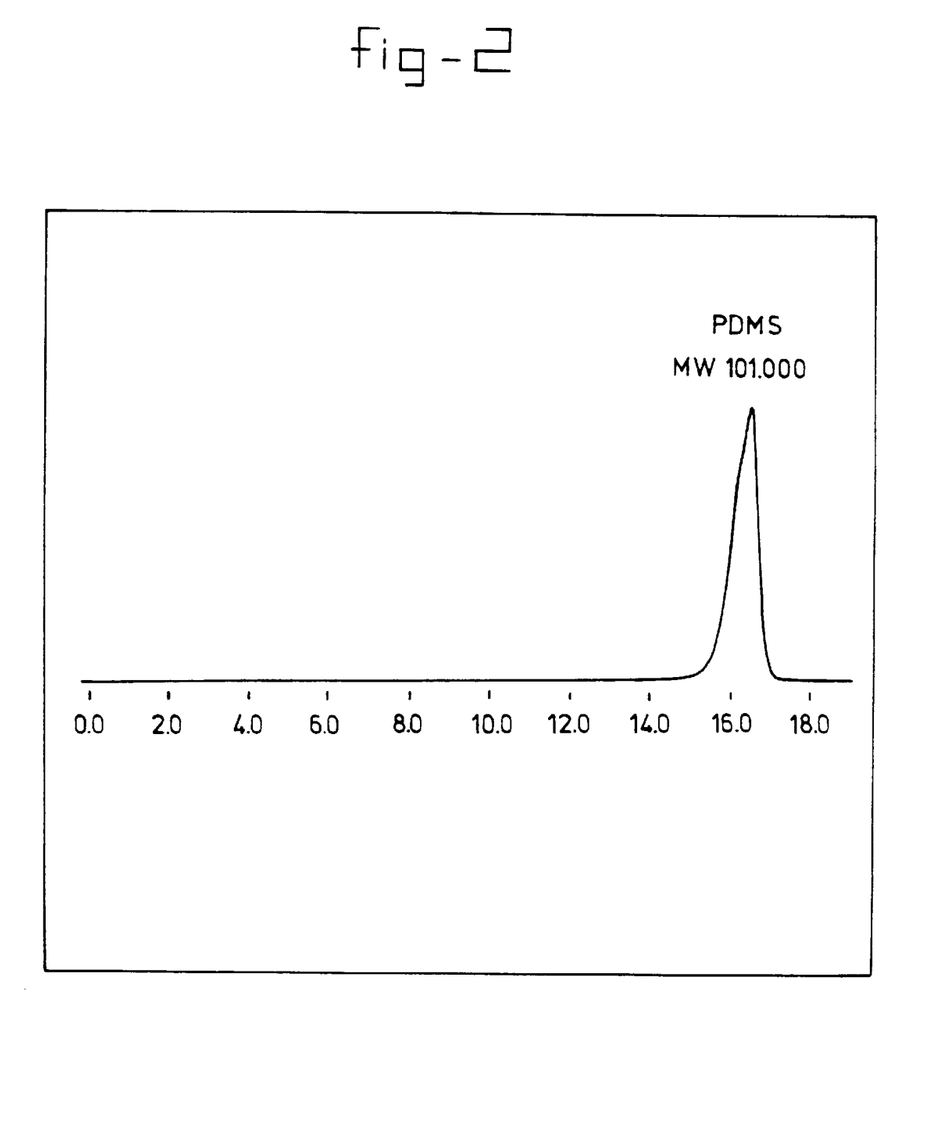
FIG. 2 depicts a chromatograph of a polymer in a THF/water mixture.

Five $\mu$l of polymer solution containing 50 mg of PDMS per ml of THF was injected and eluted using a gradient eluent starting from water/THF (50/50, v/v) to 100% THF in 15 min, at a flow of 1 ml/min. After the sample had passed the separation column, water was added to the flow, at a rate of 3 parts of water to 1 part of THF solution. The polymer was detected at a wavelength of 550 nm. The result is shown in FIG. 2. Even though PDMS gives very small differences in refractive index with the THF/water mixture, the detection is very good.

EXAMPLE 2

A mixture of polystyrene standards according tO the molecular weight was analysed using the following characteristics:

Gradient: Water/THF (50/50) to THF in 30 min.

Flow: 1 ml/min

Column: NovaPak Cyanopropyl (CN), 15 cm. 3.9 mm

Turbidity detector: UV M486: 350 nm

Turbidity pump: Water+detergent; flow 3 ml/min; room temperature

Figure 3:
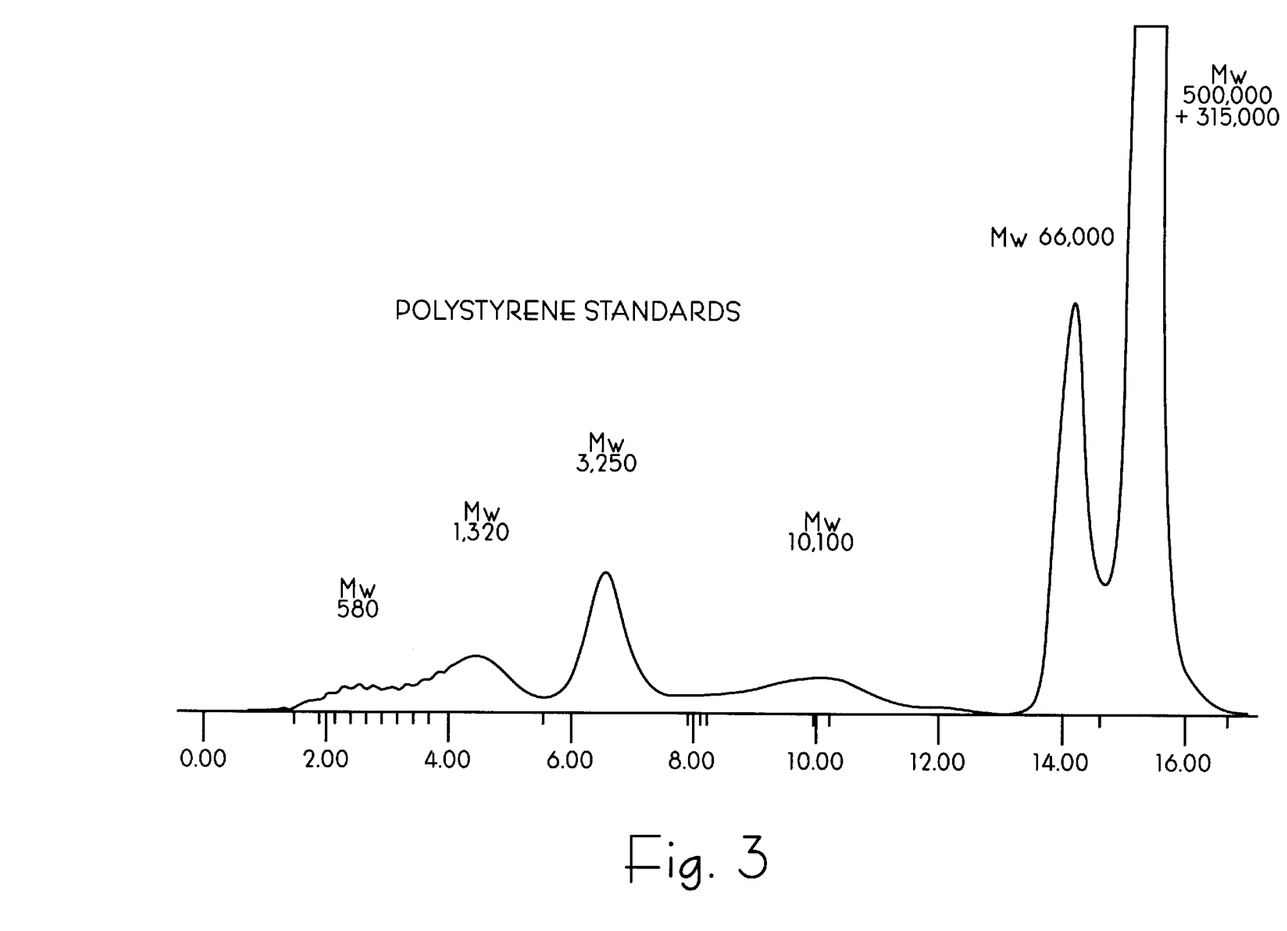
FIG. 3 depicts a chromatograph of polystyrene standards in a THF/water to THF gradient.

The results are shown in FIG. 3. This example shows that very small polymer molecules can also be detected by the system according to the invention.

EXAMPLE 3

A broad mixture of polymers [poly(vinyl acetate) (PVAC) M.W. 125,000; poly(methyl methacrylate (PMMA) M.W.

Figure 4:
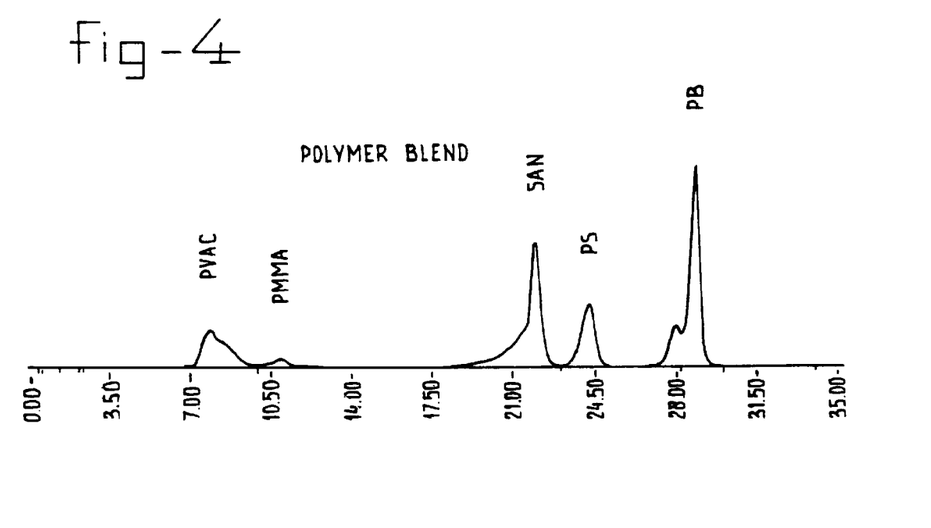
FIG. 4 depicts a chromatograph of a broad mixture of polymers in a THF/water to THF gradient.

110,000; styrene-acrylonitrile copolymer (SAN) M.W. 175,000; polystyrene (PS) M.W. 165.000; styrenebutadiene-styrene copolymer (SBS); and polybutadiene (PB) M.W. 120,000] was analysed using the following characteristics:

Gradient: Water/THF (50/50) to THF in 30 min.
Flow: 1 ml/min
Column: NovaPak Cyanopropyl (CN), 15 cm, 3.9 mm
Turbidity detector: UV M486: 350 nm
Turbidity pump: Water+detergent; flow 3 ml/min; room temperature The results are shown in FIG. 4. This example shows that the detection system according to the invention is useful as a universal detector.

EXAMPLE 4

A solution of polydimethylsiloxane (M.W. 101,000) was analysed using gel permeation chromatography (GPC) connected to a turbidity detector, according to the following characteristics:

Eluent: THF
Flow: 1 ml/min
Column: Shodex 80M 2×
Turbidity detector: UV M486: 350 nm
Turbidity pump: Water, flow 3 ml/min.

Figure 5:
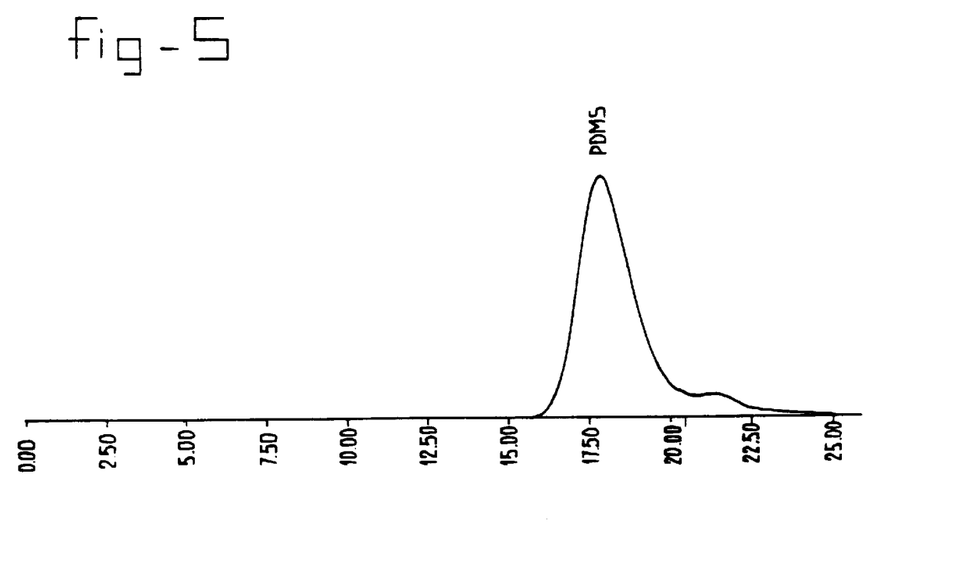
FIG. 5 depicts a chromatograph of a polydimethylsiloxane in an eluent of THF.

The results are shown in FIG. 5.

EXAMPLE 5

A solution of poiy(vinyl chloride) (PVC), a non-UV absorbing polymer having an M.W. of 120,000, was analysed using gel permeation chromatography (GPC) connected to a turbidity detector, according to the following characteristics:

Eluent: THF
Flow: 1 ml/min
Column: Shodex 80M 2×
Turbidity detector: UV M486: 350 nm
Turbidity pump: Water, flow 3 ml/min.

Figure 6:
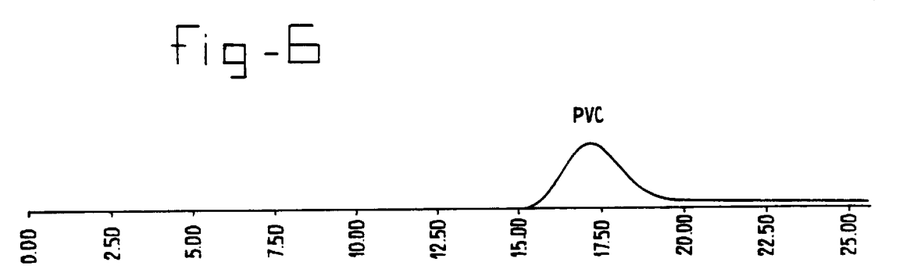
FIG. 6 depicts a chromatograph of a poly(vinyl chloride) in an eluent of THF; and, FIGS. 7–10 depict chromatographs of a polystyrene standards.

The results are shown in FIG. 6.

EXAMPLE 6

A solution of polystyrene (PS) standards was selectively analysed according to the following characteristics:

Eluent: THF
Flow: 1 ml/min
Column: GPC Shodex 80M 2×
Turbidity detector: UV M486: 350 nm
Turbidity pump: Water flow 0–1 ml/min.

Figure 7:
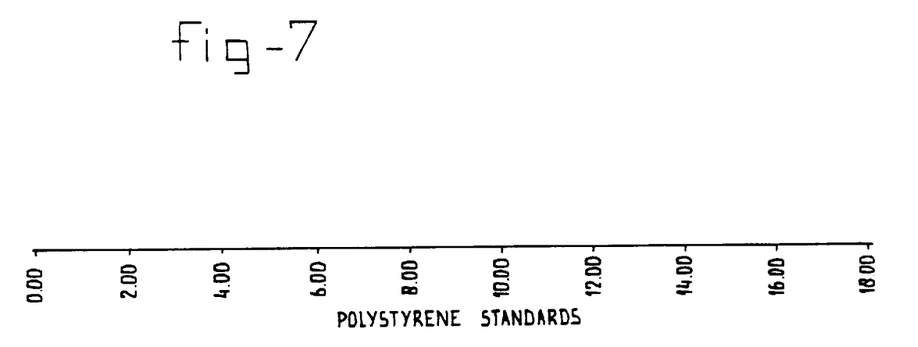
Figure 8:
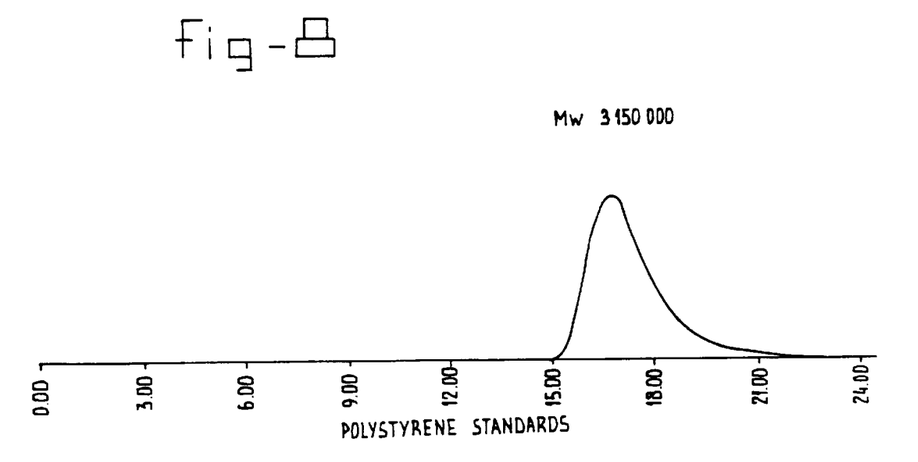
Figure 9:
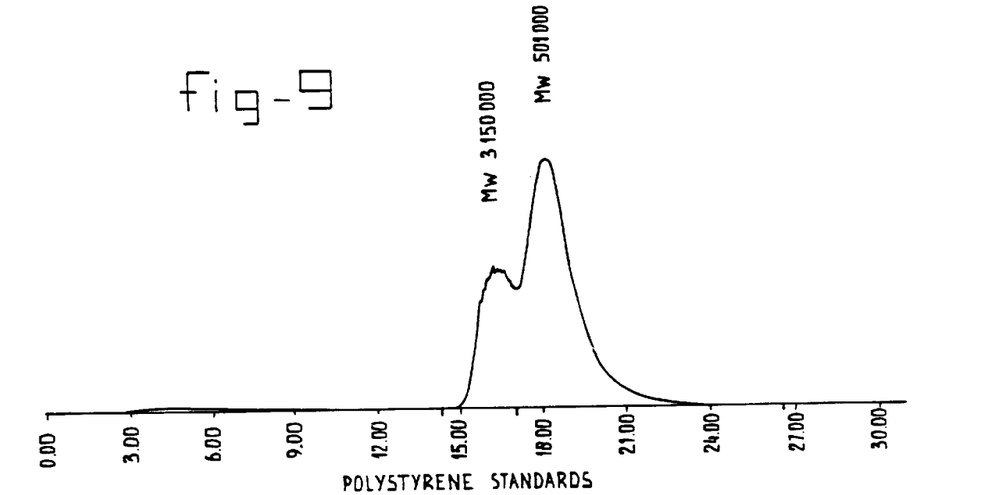
Figure 10:
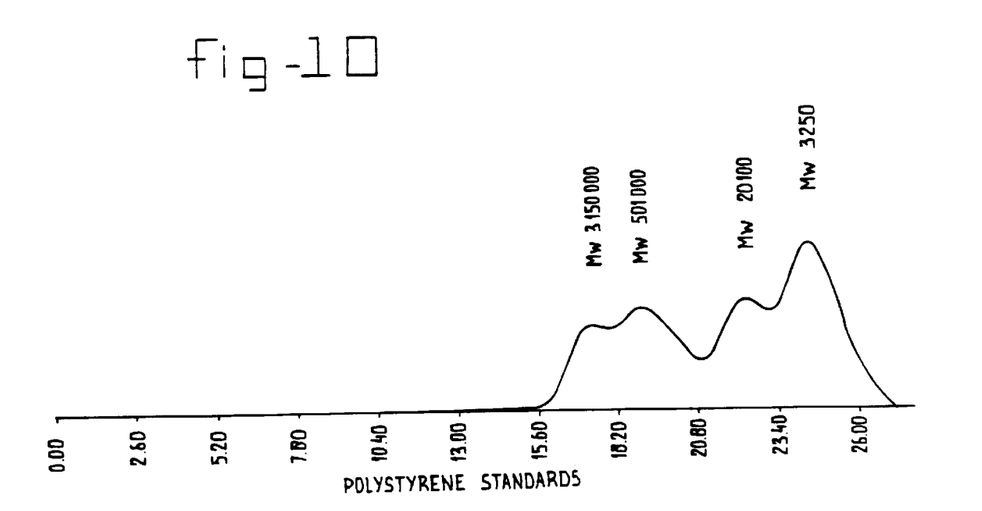

When no non-solvent was added after the separation column, no peaks for PS were visible at 350 nm (PS has a UV absorption at 260 nm), see FIG. 7. Increasing the amount of non-solvent results in the polymer having the highest molecular weight to become turbid first. The following water flows of the turbidity pump were used:

Turbidity pump: Water flow 0 ml/min (see FIG. 7)
Turbidity pump: Water flow 0.12 ml/min (10.7%) (see FIG. 8)
Turbidity pump: Water flow 0.2 ml/min (16.7%) (see FIG. 9)
Turbidity pump: Water flow 1.0 ml/min (50%) (see FIG. 10)

At a water flow of 1.0 ml/min, the proportion of non-solvent (50%) is so high that all polystyrenes are turbid and detected.

In this mode of operation the detector is a selective (tuneable) detector.

What is claimed is:

1. A method of quantitatively detecting a polymer in a solution of the polymer in a solvent, comprising the steps of (a) adding to the solution a non-solvent for said polymer in a sufficient amount to make the resulting liquid turbid, (b) measuring the turbidity of the resulting liquid, and (c) relating the turbidity of the resulting liquid to known standards which standards correlate to the concentration of the polymer.

2. The method according to claim 1, wherein the non-solvent is added to the solution in an amount sufficient to render the polymer insoluble in the resulting liquid.

3. The method according to claim 1, wherein the turbidity is measured using a UV/VIS detector, a fluorescence detector, or a laser light scattering detector.

4. The method according to any one of claims 1–3, wherein the non-solvent is added as a continuous flow to a continuous flow of polymer-containing solution.

5. The method according to any one of claims 1–3, wherein the solvent comprises tetrahydrofuran, dioxane, dichloromethane, chloroform, dimethylformamide or cyclohexane, and the non-solvent comprises water, methanol, acetonitrile, hexane or isooctane.

6. The method according to any one of claims 1–3, wherein the solvent comprises water, methanol or acetonitrile and the non-solvent comprises tetrahydrofuran, dioxane or dimethylformamide.

7. The method according to any one of claims 1–3, wherein said polymer solution is a solution resulting from a liquid chromatography step.

8. The method according to claim 7, wherein said liquid chromatography is gel permeation chromatography, size exclusion chromatography, ion chromatography, protein liquid chromatography, capillary zone electrophoresis or gradient polymer elution chromatography.

9. The method according to any one of claims 1–3, wherein the non-solvent is added after the polymer-containing solution is cooled, in particular to −10° C.

10. A device for quantitatively detecting the presence or absence of a first polymer in a solution potentially containing said first polymer and at least one other polymer, said device comprising:
 (a) a first conduit for transporting a solution potentially containing at least one polymer;
 (b) a second conduit in fluid communication with said first conduit, said second conduit containing a non-solvent in an amount to make a turbid liquid in the presence of said solution in the first conduit, as a result said first polymer forming a suspension;
 (c) a mixing chamber in fluid communication with said second conduit and said first conduit for mixing said first solution with said non-solvent to form said turbid liquid in the presence of said first polymer; and,
 (d) monitoring means in communication with said first conduit, downstream from said second conduit, for determining the presence of said turbid liquid using a UV/VIS detector, a fluorescence detector, or a laser light scattering detector, and in the presence of said turbid liquid, determining the concentration of the first polymer by isolating the first polymer from said liquid, or measuring the intensity of the turbidity and comparing said turbidity to a known standard related to the concentration of said first polymer, to quantitatively detect said first polymer.

11. The device according to claim 10, wherein the detector is a UV/VIS detector or a fluorescence detector.

12. A High Performance Liquid Chromatography apparatus comprising a liquid ration system connected to the detecting device according to claim 10 or 11.

13. The chromatography apparatus according to claim 12, wherein the separation system is a gradient polymer elution chromatography system.

14. A method of quantitatively detecting at least one polymer selected from the group consisting of a first polymer and a second polymer in a solution potentially containing the first polymer and second polymer in a solvent, said solution flowing through a conduit comprising the steps of (a) adding to the solution a non-solvent for at least one of said first polymer or said second polymer in a sufficient amount to make the resulting liquid turbid as a result of said first polymer or second polymer forming a suspension in said liquid, (b) monitoring the liquid for the presence of turbidity, and (c) relating the turbidity of the resulting liquid to at least one of the following: (i) known standards; or (ii) in the event turbidity is detected, determining the concentration of the polymer by isolating the polymer from said liquid, wherein the turbidity is measured using a UV/VIS detector, a fluorescence detector, or a laser light scattering detector to quantitatively detect said first or second polymer.

* * * * *